United States Patent [19]

Aizawa et al.

[11] Patent Number: 5,198,367
[45] Date of Patent: Mar. 30, 1993

[54] HOMOGENEOUS AMPEROMETRIC IMMUNOASSAY

[76] Inventors: Masuo Aizawa, 2-19-4 Amanuma, Suginami-ku, Tokyo 167, Japan; Brenda D. Manning, 158 Canton St., North Easton, Mass. 02356; Miki Hidaka, 2040 Pelham Ave., Los Angeles, Calif. 90025; Laura S. Uretsky, 9-1 Shadowbrook La., Milford, Mass. 01757

[21] Appl. No.: 364,731

[22] Filed: Jun. 9, 1989

[51] Int. Cl.$^5$ ................... G01N 33/536; G01N 33/543
[52] U.S. Cl. ..................................... 436/518; 435/817; 436/537; 436/538; 436/544; 436/806; 436/817; 436/818; 530/363; 530/807; 530/812
[58] Field of Search ...................... 422/82.01; 435/817; 436/537, 538, 518, 544, 806, 818, 817; 530/350, 363, 807, 812

[56] References Cited

U.S. PATENT DOCUMENTS

| | | | |
|---|---|---|---|
| 4,233,144 | 11/1980 | Pace et al. ............................ | 436/544 |
| 4,882,013 | 11/1989 | Turner et al. ......................... | 435/817 |
| 5,053,497 | 10/1991 | Hwang et al. ......................... | 436/829 |

FOREIGN PATENT DOCUMENTS 0142301  5/1985  European Pat. Off. .

OTHER PUBLICATIONS

Heineman et al., Analytical Chemistry 57(12) pp. 1321–1331 (1985).
Chemical Abstracts 105(15) p. 354 (No. 130350m) (Oct. 13, 1986) (note JP-A-61100660 (May 1986)).
Mizutani et al., "Ferrocene-attached bovine serum albumin as a mediator between glucose oxidase and an electrode", Denki Kagaku oyobi Kogyo Bitsuri Kagaku, 1988, vol. 56, pp. 1100–1101, (Abstract).

*Primary Examiner*—David Saunders
*Assistant Examiner*—Christopher L. Chin
*Attorney, Agent, or Firm*—Nicholas I. Slepchuk, Jr.; Arthur S. Morgenstern

[57] ABSTRACT

A method is described for measuring the amount of analyte present in a sample containing the analyte using a homogeneous amperometric immunoassay. The analyte is covalently bonded to a suitable carrier molecule, which is also covalently bonded to an electroactive molecule. The electroactive molecule, such as ferrocene carboxylic acid, contains a redox center which is capable of transferring a charge to an electrode. A preferred carrier molecule is bovine serum albumin (BSA), while suitable analytes include digoxin, theophylline and HCG. The immunoassay is conveniently performed by applying a voltage to a set of electrodes.

19 Claims, No Drawings

HOMOGENEOUS AMPEROMETRIC IMMUNOASSAY

BACKGROUND OF THE INVENTION

The present invention relates to an electrochemical immunoassay which can be used for detecting the presence of analytes such as digoxin, theophylline, creatine kinase (CKMB) and human chorionic gonadotrophin (HC). The improvement of this invention involves the use of a complex comprising an electroactive molecule, a carrier molecule and the analyte of interest, in a homogeneous immunoassay.

Electrochemical detection methods are widely employed in the clinical diagnostic market since these methods are relatively inexpensive and simple to use. Heterogeneous electrochemical immunoassay systems frequently require a high degree of operator involvement, due to extensive washing steps and multiple reagent additions, when sensitivities of better than $10^{-6}$M are desired. Even this level of sensitivity is insufficient for the detection of smaller analytes of clinical significance, such as digoxin, and the detection of most larger analytes such as CKMB and HCG. For instance, digoxin, which is a cardiac glycoside widely used for treating congestive heart failure and other acute cardiac conditions, is a potent drug having a therapeutic effect at concentrations as low as 1 nmol/L with a small therapeutic index. However, digoxin can also be toxic at low concentrations, with the dosage required to produce therapeutic effects and the sensitivity to toxicity being dependent on the particular patient undergoing treatment. Rapid detection of digoxin in the nanomolar range is required for treating cardiac patients, and any useful detection method for digoxin must be capable of measuring nanomolar concentrations with a rapid response time. These problems could be solved by employing a homogeneous system of higher sensitivity, but to date the development of such a system has been elusive. The difficulty in developing such systems based on nonenzymatic electroactive labelling for electrochemical immunoassays is described by W. R. Heineman et al in *Methods of Biochemical Analysis*, 32, pages 345-393 (1986).

The use of homogeneous electrochemical immunoassays for detecting the presence of theophylline has been reported in M. Haga et al in *Analytical Biochemistry*, 118, pages 286-293 (1981), using a liposome immunosensor employing liposomes which contain entrapped enzymes whose activity is directly proportional to the lysis of the liposome and inversely proportional to the concentration of free antigen in the sample. When a current pulse is introduced into the sample, the enzyme catalyzes the depletion of oxygen which is detected by an oxygen electrode, and the current registered. The incorporation of electroactive molecules within liposomes is reported in R. M. Kannuck et al in *Analytical Chemistry*, 60, pages 142-147 (1988), which describes the encapsulation of potassium ferrocyanide within liposomes for signal amplification. The liposome binds with an antibody present in the sample, releasing the encapsulated potassium ferrocyanide, which transmits a charge to the electrode surface. Electroactive liposome technology, while of theoretical interest, is difficult to utilize in practice and can produce false readings due to the instability of the liposomes employed in such systems.

The use of both heterogeneous and homogeneous immunoassay systems involving electroactive enzyme complexes is also described in G. A. Robinson et al, Journal of Immunoassay, 7, pages 1-15 (1986) and in European Patent Application No. 85303367.8, filed May 13, 1985. This technology is directed to the detection of thyroxine by employing a conjugate of thyroxine and ferrocene monocarboxylic acid. The conjugate functions as an electron transfer mediator between an oxido-reductase enzyme, such as glucose oxidase, and an electrode. The ability of the conjugate to function as an electron transfer mediator is impaired by the presence of an anti-thyroxine antibody which binds to the conjugate reducing the current flow to the electrode. In the homogeneous mode, all of the necessary components of system including the conjugate, antibody, thyroxine, glucose oxidase and glucose are initially present or added to the sample. Alternatively, the heterogeneous mode contains the enzyme and antibody which are co-immobilized on the electrode. This system has the disadvantage of being subject to interference, such as interference from oxygen which is present and not purged from the system, or the production of hydrogen peroxide as a side reaction product. Moreover, the additional requirement of enzyme reaction and diffusion necessitates an increased response time for this system, as well as the requirement for measuring both the baseline activity, and the activity level after the additional of sample.

Similarly, both H. M. Eggers et al, *Clinical Chemistry*, 28, pages 1848-1851 (1982), and T. T. Ngo et al, *Applied Biochemistry and Biotechnology*, 11, pages 63-70 (1984), describe electrochemical immunoassay techniques for detecting the presence in samples of NADH and DNP-aminocaprodoic acid, respectively. Both of these methods have many of the same disadvantages as the methods discussed previously, and in addition sensitivities of only $10^{-6}$M are thought to be possible using these approaches.

Chemically-modified enzymes which are capable of directly participating in oxidation/reduction reactions are described by Y. Degani and A. Heller in *The Journal of Physical Chemistry*, 91, pages 1285-1289 (1986), *Journal of the American Chemical Society*, 110, pages 2615-2620 (1988), and in European Patent Application No. 88300814.6, filed Feb. 1, 1988. The technology described in these publications involves the reaction of enzymes such as glucose oxidase and D-amino acid oxidase with ferrocene carboxylic acid to form a complex which contains a redox center. The complex is capable of direct electrical interaction with an electrode. Alternatively, the tyrosine groups of glucose oxidase can be transformed into electrochemically active groups, such as DOPA groups, permitting the same interaction. The presence of glucose in a sample is determined by directly measuring the current at the electrode due to the reaction of glucose with the modified enzyme.

As pointed out in European Patent Application No. 88300814.6, the electrolytic modification of an enzyme to incorporate a redox center or couple, while theoretically desirable is usually difficult to achieve. Attempted modifications of enzymes can readily lead to deactivation, such as the attempted modification of carboxy groups in bovine carboxypeptidase A with N-ethyl-5-phenylisoxazolium-3′sulphonate. As indicated in the European patent application, the presence of the redox center in the modified enzyme is believed to be critical since the redox center must be close enough to the electrode to permit electron transfer, while sufficiently removed from the chemical center to avoid deactivation of the enzyme. It will be appreciated that in practice this is a difficult condition to achieve.

SUMMARY OF THE INVENTION

In accordance with the present invention, an electroactive complex is provided which comprises at least one antigenic analyte covalently bonded to a carrier molecule which is also covalently bonded to at least one electroactive molecule. Preferably, the analyte is digoxin, the carrier molecule is bovine serum albumin, and the electroactive molecule is ferrocene carboxylic acid. The electroactive complex is combined with a sample of biological fluid, such as blood, in an electrolytic cell which also contains predetermined amounts of an antibody to the analyte. Differential pulse voltammetry is used to determine the peak current caused by the complex in the sample fluid. This current is compared to standard curves generated using known amounts of analyte, antibody and electroactive complex to determine the concentration of antigen present in the sample.

DESCRIPTION OF THE PREFERRED EMBODIMENTS

The homogeneous amperometric immunoassay of this invention is a competitive immunoassay which involves the competitive binding of an electroactive conjugate or complex containing the antigen or analyte as a component thereof with free antigen in a sample for binding to an antibody specific for the antigen. The electroactive complex is capable of transferring electrons to electrodes which are inserted in a sample of a biological fluid, such as human blood or serum, also containing the electroactive complex. However, upon introduction of an antibody specific to the analyte or antigen in the sample, the electroactive complex is bound and thereby prevented or inhibited from transferring electrons to the electrode. This reaction is reversible in a competitive binding environment since the introduction of free analyte in the sample, or the presence of free analyte in the sample, competes with the complex-bound antigen for antibodies. It is believed that the complex is deactivated due to stearic hinderance of the complex, by the antibody or that diffusion to the electrode is slower due to the increased size of the antibody bound complex. In this sense, the immunoassay technique employed in this invention is similar to a classical competitive binding assay except that the present system can be conveniently adapted for electrolytic measuring techniques.

In carrying out the present invention, three electrodes are contacted with the sample of biological fluid in a suitable container. Physical contact is generally made by immersing the electrodes in the sample. Both the working electrode and the counter electrode are generally metal electrodes formed from gold or platinum or graphite electrodes. Convenient reference electrodes include $Hg/Hg_2Cl_2$ and $Ag/AgCl$ in chloride ion-containing solutions.

The sample generally contains an unknown amount of analyte which is to be determined using the present detection technique. A predetermined amount of electroactive complex and an antibody to the antigen are added to a fixed amount of sample. A voltage is applied across the electrodes and the current through the sample solution is measured. The voltage is applied using differential pulse voltammetry whereby small amplitude pulses of voltage are applied over a certain voltage range. The current is sampled both just before and after the pulse and the output signal is the current difference. From this data the peak current obtained over the voltage range can be determined. This peak current is compared to standard or reference curves which are generated by using known amounts of antigen with the same predetermined amount of electroactive complex and antibody in an appropriate matrix. The amount of antigen present in the original sample is then conveniently determined from the standard curve.

Typical analytes which are useful in the present invention for preparing the electroactive complex and which are suitable for measurement in a sample fluid include digoxin, theophylline, HCG and CKMB. These analytes are all capable of being covalently bound to a suitable carrier molecule, such as bovine serum antibody (BSA), which is also bound to an electroctive molecule such as ferrocene carboxylic acid. The covalent attachment of a digoxin molecule to a ferrocene/BSA conjugate is described in more detail in Example 1. While Example 1 is specific for the reactants described therein, it should be appreciated that the preparatory technique is applicable to any analyte which is capable of such covalent attachment. More than one analyte can be attached to the carrier molecule, if desired, resulting in multiple binding sites for the antibody and enhanced inhibition and inactivation of the electroactive complex.

Digoxin is a preferred analyte since it is widely used in clinical environments and can be chemically modified for covalent attachment to a carrier molecule through the formation of Schiff's bases followed by reduction of the digoxin molecule. Since digoxin is only sparingly soluble in aqueous solutions, it is desirable that any electroactive complex which incorporates one or more molecules of digoxin be at least as soluble, and preferably more soluble, than digoxin alone. Although digoxin has been specifically illustrated in the accompanying examples, it should be appreciated that this invention is also applicable to a wide range of suitable analytes of clinical interest, provided that the analytes can be chemically modified to incorporate amino or carboxyl groups, and can therefore be covalently bound to the carrier molecule, and that the electroactive complex formed from the analyte is soluble in the sample medium. It is also necessary for the analyte to have a corresponding antibody which is capable of binding to the analyte and to the analyte component of the electroactive complex. Upon attachment to the analyte portion of the electroactive complex, the complex should be electrically deactivated so that the transfer of electrons from the complex to the electrode is substantially impeded. Antibodies selective for digoxin have a high affinity constant and are therefore useful in competitive assays containing free digoxin and electroactive complex. Amounts of analyte which can be present in the sample will vary depending on the normal dosage range of the analyte which is used for therapeutic purposes. Digoxin, which is a highly potent drug, is typically present in amounts of from about 0.5 nanograms/ml of sample to about 2.0 nanograms/ml of sample.

The electroactive molecule is a molecule which contains a redox center and is capable of transferring electrons to the electrode. Typical electroactive molecules include the ferrocene derivatives, such as ferrocene carboxylic acid and ferrocenylacetic acid. The electroactive molecule must also be capable of being covalently bound to a suitable carrier molecule without thereby losing the capability of transferring a charge to the electrode. Ferrocene carboxylic acid is a particularly preferred electroactive molecule. If desired, more than one electroactive molecule can be covalently bound to the carrier molecule to produce an amplification effect resulting in a higher amperometric response than obtainable with a single electroactive molecule. Ferrocene derivatives are preferred electroactive molecules since they have excellent electrochemical properties, including redox activity over a wide potential range, reversibility, pH independence, non-autooxidation, low solubility in the reduced form and a high solubility in the oxidized form.

The electroactive complex can be prepared by any suitable means which provides for the covalent attachment of the electroactive molecule, the carrier molecule and the antigenic analyte. Example 2 illustrates the preparation of a ferrocene-BSA-digoxin complex which contains multiple ferrocene and digoxin molecules linked by a single BSA molecule. In the procedure disclosed in this example, ferrocene groups are first bound to a molecule of BSA using ferrocene carboxylic acid as a reactant to form a conjugate, and multiple digoxin groups are then bound to the BSA part of the conjugate.

The use of a carrier molecule, such as BSA, to form the electroactive complex has been found to be essential in the practice of this invention. The omission of the intermediate carrier or linking molecule was attempted during the synthesis of a ferrocene-digoxin molecule, but during the synthesis a ferrocene derivative was produced which was found to be insoluble in the sample. The use of BSA, which is a plasma protein regulating the osmotic pressure of blood, ha the advantage of being highly soluble in aqueous solutions, having an intrinsic buffering action, and containing a large number of hydrophilic amino group residues which permit covalent modification and the attachment of more than one ferrocene and digoxin molecule to a single BSA molecule. Although BSA is a preferred carrier molecule, other carrier molecules which are readily soluble in a sample of interest can also be used, such as cytochrome C or ribonuclease.

The electroactive complex and antibody should also be compatible with any additional components which may be added to the sample such as buffering agents and stabilizers. Typically, the sample fluid will be buffered to a pH within the range of 6.5 to 7.5, depending on the particular test which is to be run.

The homogeneous amperometric immunoassay of this invention has been found to have a high level of sensitivity which is useful in the measurement of small quantities of analytes, while employing the lower level of operator involvement limited to less sensitive immunoassays to date.

The following examples are intended to illustrate various embodiments of the present invention without limiting it thereby. Modifications and departures from the examples may be made without departing from the spirit and scope of the invention as will be readily understood by those skilled in the art.

EXAMPLE 1

A ferrocene-BSA conjugate was prepared using the general procedure described by Y. Degani and A. Heller in the *Journal of Physical Chemistry* (1987), except that BSA was substituted for glucose oxidase.

Ferrocene carboxylic acid, 80 mg, was ground in a small mortar and pestle to a fine powder. It was then dissolved by adding a minimal amount of 0.15 M Na-Hepes buffer a few drops at a time. Two ml was usually sufficient if the powder was finely ground. The Hepes buffer was left unadjusted for pH until the powder was dissolved. The solution of ferrocene carboxylic acid was transferred to a 25 ml sample bottle containing a magnetic stirring bar, and all containers were rinsed with fresh buffer until the total volume equaled about 4 ml. The sample bottle was immersed in an ice bath, set up for pH monitoring with stirring and the pH was adjusted to 7.3 by adding 0.1M HCl dropwise. During all of the remaining steps, the pH was maintained between 7.2–7.3 by adding either 0.1M HCl or 0.15M Na-Hepes dropwise. [1-(3-dimethylaminopropyl)-3-ethylcarbodiimide hydrochloride], 100 mg, was added and the solution stirred for 30 minutes. Then 810 mg of urea was added with an additional 15 minutes of stirring. The stirring speed was increased to create a visible vortex while 250 mg of BSA was added gradually, allowing each added amount to dissolve completely before the next addition to avoid clumping. The solution became relatively homogeneous and viscous. Stirring continued for 30 minutes after all of the BSA had been dissolved. The sample bottle was covered with paraffin and set in a refrigerated Dewar flask at 4° C. for 18 hours. If left too long, the reaction continues and a coagulated mass results. The mixture was centrifuged at a low speed for 15 minutes after transfer a centrifuge tube. The turbid supernatant was filtered under slight pressure (2 atm) through a 0.2 micron pore filter.

The conjugate was purified from the starting reactants by passage through a 1.5 cm×20 cm Sephadex G-15 gel chromatography column. The gel column was equilibrated and eluted with sodium phosphate buffer, pH 7.0. Fractions of 2 ml volume were collected and the orange conjugate was eluted at about the 13th of 25 fractions collected. The identity of the conjugate was verified by absorbence maxima: 280 nm for BSA and 450 nm for ferrocene carboxylic acid. The electroactivity of the conjugate was confirmed by cyclic and differential pulse voltammograms obtained on a standard three electrode system using platinum counter and working electrodes and an Ag/AgCl reference electrode with a potentiostat (Table 1).

EXAMPLE 2

A ferrocene-BSA-digoxin complex was prepared using the general procedure described in V. P. Butler et al, *Methods in Enzymology* (1982).

Digoxin, 50 mg, was ground to a fine powder using a mortar and pestle. The powder was then mixed with a minimal amount of 95% ethanol (less than 1 ml). After transfer to a 25 ml sample bottle with rinsing of the mortar and pestle with additional ethanol (1 ml), the mixture had a milk of magnesia consistency. Freshly prepared 0.1M $NaIO_4$, 2 ml, was added to the mixture dropwise over 5 minutes with continuous stirring. The stirring was then continued for 30 more minutes. Ethylene glycol, 0.1 ml, was added to stop the reaction and deactivate excess unreacted $NaIO_4$ and stirring was continued for 5 minutes. The pH of the mixture was then adjusted to 9.3–9.5 by the addition of 5% $K_2CO_3$ dropwise and the purified ferrocene-BSA conjugate was added all at once. Maintaining the pH in the 9.3–9.5 by the addition of 5% $K_2CO_3$, stirring was continued for 45-60 minutes or until the pH remained stable for 20 minutes. Freshly dissolved $NaBH_4$, 30 mg in 2 ml of deionized water was added to the mixture, the bottle was covered with foil loosely to allow gas evolution and left to stand 18 hours at room temperature. At the end of this time, 1M formic acid was added until the pH reached 6.5 and then the mixture stood at room temperature for 1 hour. Stirring was resumed and 1M $NH_4OH$ was added dropwise until the pH reached 8.5.

The ferrocene-BSA-digoxin complex was purified from the starting reactants by passage through the same type of column as that used for the ferrocene-BSA conjugate purification. At least 35 fractions of 2 ml each were collected. The digoxin containing fractions were identified by noting the color change of 200 microliter samples of each fraction when added to 1 ml of $H_2SO_4$. Digoxin turns reddish-brown in concentrated $H_2SO_4$ and fractions 21-26 were found to contain digoxin. As done previously the electroactivity of the complex was determined for these fractions (Table 1).

TABLE 1

|  | E½ | cathodic peak | anodic peak |
|---|---|---|---|
| ferrocene-carboxylic acid | 330 mV | 290 mV | 370 mV |
| ferrocene-BSA conjugate | 480 mV | 430 mV | 530 mV |
| ferrocene-BSA-digoxin complex | 480 mV | 380 mV | 580 mV |

EXAMPLE 3

Polyclonal antidigoxin antibody was added to the ferrocene-BSA-digoxin complex in 0.085M $NaHPO_4$ buffer, pH 7.0 and incubated for 20 minutes at 37° C. The added antibody caused a 40% decrease in cathodic current. The addition of free digoxin, restored the cathodic current to the original value.

EXAMPLE 4

The peak oxidation current for the ferrocene-BSA-digoxin complex, $10^{-8}$M, in a 1 ml phosphate buffer sample volume was measured by differential pulse voltammetry. A 10 ul aliquot of polyclonal antidigoxin antibody was added to the complex and mixed for 20 minutes. The peak oxidation current was again measured. Then 50 ul of various concentrations of digoxin standards were added with mixing for 20 minutes after which peak oxidation currents were again measured. The experiment performed in this way shows a dynamic range for digoxin concentration of 100-300 ng/ml which corresponds to $1 \times 10^{-7}$ to $4 \times 10^{-7}$M digoxin. Further experimentation was limited by the amount of electro-active complex available but the use of a more dilute complex sample made it possible to detect a 50 ng/ml ($6 \times 10^{-8}$M) digoxin standard.

The above experiments were performed with a complex that was about 6 months old and had been stored in buffer at 4° C. during that time. The detection limit achieved and the current measured with this complex which was found to have a 14:1 ferrocene to BSA ratio. The detection limit achieved with a freshly made complex having a 1:1 ferrocene to BSA ratio. It was observed that the current obtained for the 14:1 complex is about the same as that obtained for the 1:1 complex and that the detection limit for the 1:1 complex is 100 times lower. Although the 14:1 complex would be expected to have a lower detection limit compared to that of the 1:1 complex, the actual experimental difference in the detection limit is attributable to the difference in freshness of each sample and to the subsequent loss in activity of the 14:1 complex over time.

The current detection limit indicated in the examples demonstrates that many therapeutic drugs can be assayed using this technique (See Attached Table 2). All compounds above the $5 \times 10^{-8}$M concentration range would be detectable with this method. In addition, the actual concentration of digoxin in the sample being measured is 20 fold more dilute than indicated by the dose response curve due to the dilution factor of adding 50 ul of standard to the sample matrix. This means that the actual detection limit is $5 \times 10^{-9}$M. Either more sample that 50 ul can be used, or preferably the assay can be performed on undiluted samples.

TABLE 2

|  | Therapeutic Range (μg/dl) | Molarity |
|---|---|---|
| Theophylline | 1000-2000 | $5.6 \times 10^{-5}$-$1.1 \times 10^{-4}$ |
| Dilantin | 1000-2000 | $4 \times 10^{-5}$-$8 \times 10^{-5}$ |
| Digoxin | 0.08-0.2 | $1 \times 10^{-9}$-$2.6 \times 10^{-9}$ |
| Tobramycin | 500-1000 | $1.1 \times 10^{-5}$-$2.1 \times 10^{-5}$ |
| Gentamicin | 500-1000 | $1.1 \times 10^{-5}$-$2.1 \times 10^{-5}$ |
| Phenobarbital | 1500-4000 | $6.5 \times 10^{-5}$-$1.7 \times 10^{-4}$ |
| Lidocaine | 150-500 | $6.4 \times 10^{-6}$-$2.1 \times 10^{-5}$ |
| Quinidine | 200-500 | $6.2 \times 10^{-6}$-$1.5 \times 10^{-5}$ |

EXAMPLE 5

Examples 1 and 2 present well-known methods for conjugating molecules having the appropriate functional groups. Carrier molecules having either amino or carboxyl groups can be coupled to the corresponding electroactive molecules or analytes with amino or carboxyl groups using the carbodiimide procedures shown in Example 1. In order to demonstrate the general application of the complex synthesis procedures we have made the following complexes that exhibit similar properties to the BSA complex discussed in the previous examples.

TABLE 3

|  | Cathodic Peak | Anodic Peak |
|---|---|---|
| Ferrocene carboxylic acid | 290 mV | 350 mV |
| Ferrocene-BGG-digoxin[a] | 280 mV | 330 mV |
| Ferrocene-BSA-digoxin | 380 mV | 430 mV |
| Ferrocene-RNase-digoxin[b] | 380 mV | 440 mV |

[a]BGG is bovine gamma globulin
[b]RNase is ribonuclease

More control over the incorporation of electroactive molecules into the carrier molecule can be obtained if the carrier molecule is smaller than the 67,000 molecular weight BSA used in our examples. Thus, such molecules as cytochrome C, insulin, ribonuclease, or synthetic peptides may be successfully employed for carrier molecules (Table 4).

TABLE 4

| Protein | MW × $10^3$ | $NH_2$ groups | COOH groups |
|---|---|---|---|
| BSA | 66.5 |  |  |
| ribonuclease | 14.0 | 11 | 11 |
| cytochrome C | 13.0 | 20 | 13 |
| insulin | 5.7 | 2 | 5 |

All of the molecules in Table 4 are small proteins known to be soluble in physiological solutions. In addition, using a smaller molecular weight carrier molecule enables antibody molecules (molecular weight=150,000) to affect electroactivity of the complex to a greater extent. The protein antigens such as HCG can also contain these amino and carboxyl groups, and therefore can be coupled to the carrier molecule via the carbodiimide protocol. Maintenance of antibody binding ability by the antigen can be enhanced by performance of the coupling in the presence of bound specific antibody followed by the dissociation of the antigen/antibody complex.

What is claimed is:

1. A method for determining the concentration of an analyte present in a sample of biological fluid contained in an electrochemical cell equipped with a set of electrodes, said method comprising the steps of:
    a) forming an electroactive complex containing an antigenic analyte covalently bonded to a carrier molecule, said carrier molecule also being covalently bonded to an electroactive molecule capable of transferring a charge to an electrode,
    b) adding the biological fluid, predetermined amounts of the electroactive complex, and an antibody to the analyte to the cell,
    c) applying a voltage across the electrodes and measuring the current in the fluid at different voltage levels to form a voltage/current relationship for the sample fluid, and
    d) comparing the voltage/current relationship for the sample fluid with standard voltage/current relationships generated using known amounts of analytes to determine the concentration of analyte present in the sample.

2. The method of claim 1 wherein the analyte is selected from the group consisting of theophylline, thryoxine, digoxin and HCG.

3. The method of claim 1 wherein the carrier molecule is bovine serum albumin.

4. The method of claim 1 wherein the electroactive molecule is a ferrocene derivative.

5. The method of claim 4 wherein the ferrocene derivative is selected from the group consisting of ferrocene carboxylic acid and ferrocenylacetic acid.

6. The method of claim 5 wherein the ferrocene derivative is ferrocene carboxylic acid.

7. The method of claim 1 wherein the analyte is digoxin, the antibody is a anti-digoxin antibody, the carrier molecule is bovine serum albumin, and the electroactive molecule is ferrocene carboxylic acid.

8. The method of claim 1 wherein the working and counter electrodes are fabricated from platinum or graphite.

9. The method of claim 1 wherein the biological fluid is whole blood, plasma, serum or urine.

10. The method of claim 1 wherein a buffer is added to the fluid sample.

11. An electroactive complex, comprising at least one antigenic analyte covalently bonded to a carrier molecule, said carrier molecule also being covalently bonded to at least one electroactive molecule.

12. The electroactive complex of claim 11 wherein the analyte is selected from the group consisting of theophylline, thyroxine, digoxin, and HCG.

13. The electroactive complex of claim 11 wherein the carrier molecule is bovine serum albumin.

14. The electroactive complex of claim 11 wherein the electroactive molecule is ferrocene carboxylic acid.

15. The electroactive complex of claim 11 wherein the analyte is digoxin, the carrier molecule is bovine serum albumin, and the electroactive molecule is ferrocene caroboxylic acid.

16. The electroactive complex of claim 15 which is prepared by first covalently binding ferrocene carboxylic acid to bovine serum albumin, and subsequently covalently binding digoxin to the bovine serum albumin.

17. The electroactive complex of claim 11, wherein the carrier molecule is selected from the group consisting of bovine serum albumin, bovine gamma globulin, ribonuclease, cytochrome C, and insulin.

18. The electroactive complex of claim 11, wherein the carrier molecule is a molecule having a molecular weight less than 150,000.

19. The electroactive complex of claim 11, wherein the carrier molecule is selected from a molecule having 1 or more amino groups and/or 1 or more carboxyl groups.

* * * * *